US005470962A

United States Patent [19]
Ogawa et al.

[11] Patent Number: 5,470,962
[45] Date of Patent: Nov. 28, 1995

[54] OLIGOSIALYL-1,2-DIALKYL-SN-GLYCEROLS AND SYNTHETIC INTERMEDIATES FOR THEIR PREPARATION

[75] Inventors: Tomoya Ogawa; Shigeki Nunomura, both of Wako; Mamoru Sugimoto, Tokyo, all of Japan

[73] Assignees: Rikagaku Kenkyusho, Wako; Mect Corporation, Tokyo, both of Japan

[21] Appl. No.: 108,672

[22] PCT Filed: Mar. 3, 1992

[86] PCT No.: PCT?JP92/00249

§ 371 Date: Sep. 7, 1993

§ 102(e) Date: Sep. 7, 1993

[87] PCT Pub. No.: WO92/15599

PCT Pub. Date: Sep. 17, 1992

[30] Foreign Application Priority Data

Mar. 4, 1991 [JP] Japan .................................. 3-037594

[51] Int. Cl.$^6$ .................................................. C07H 5/06
[52] U.S. Cl. ........................ 536/17.2; 536/17.5; 536/18.5
[58] Field of Search ........................... 536/18.7, 22, 121, 536/120, 17.2, 17.5, 18.5; 514/25, 42, 53, 54, 61

[56] References Cited

U.S. PATENT DOCUMENTS 4,694,076  9/1987  Ogawa et al. ........................ 536/17.2

FOREIGN PATENT DOCUMENTS 59-164798  9/1984  Japan .
62-273992  11/1987  Japan .

OTHER PUBLICATIONS

Tetrahedron, vol. 46, No. 1, 1990 Tomoya Ogawa et al: "Highly Stereoselective Glycosylation of Sialic Acid Aided by Stereocontrolling Auxiliaries", pp. 89–102.
J. Am. Chem. Soc., 1989, 111, Yukishige Ito et al: "Highly Stereoselective Synthesis of Ganglioside GD$_3$i", pp. 8508–8510.
Journal of Biological Chemistry, vol. 240, No. 1, Jan. 1965, Erich Baer et al: "Phosphonolipids—Synthesis of Dialkyl L–α–Glyceryl–(2–Aminoethyl)Phosponates", pp. 44–48.
Biochemistry, vol. 2, No. 2, 1963, M. Kates et al: "Aliphatic Diether Analogs of Glyceride–Derived Lipids—Synthesis of D–α,β–Dialkyl Glyceryl Ethers", pp. 394–397.
Agric. Biol. Chem., vol. 46, No. 1, 1982, Tomoya Ogawa et al: "Synthesis of 3–O–Glycosyl–1, 2–Di–O–Tetradecyl–sn–Glycerol", pp. 255–262.
Tetrahedron Letters, vol. 29, No. 32, 1988, Yukishige Ito et al: "Highly Stereoselective Glycosylation of N–Acetylneuraminic Acid Aided by a Phenylthio Substituent as a Stereocontrolling Auxiliary", pp. 3987–3990.
J. Org. Chem., vol. 57, 1992, Yukishige Ito: "Studies Directed Toward the Synthesis of Polysialogang–Liosides: The Regio–and Stereocontrolled Synthesis of Rationally Designed Fragments of the Tetrasialoganglioside GQ$_{1b}$", pp. 1821–1831.
A. L. Lehninger "Biochemistry" second edition, Worth Publishers, Inc., New York, 1975, p. 287.

*Primary Examiner*—Douglas W. Robinson
*Assistant Examiner*—Kathleen Kahler Fonda
*Attorney, Agent, or Firm*—Oblon, Spivak, McClelland, Maier & Neustadt

[57] ABSTRACT

An oligosialyl-1,2-dialkyl-sn-glycerol represented by the following formula (I):

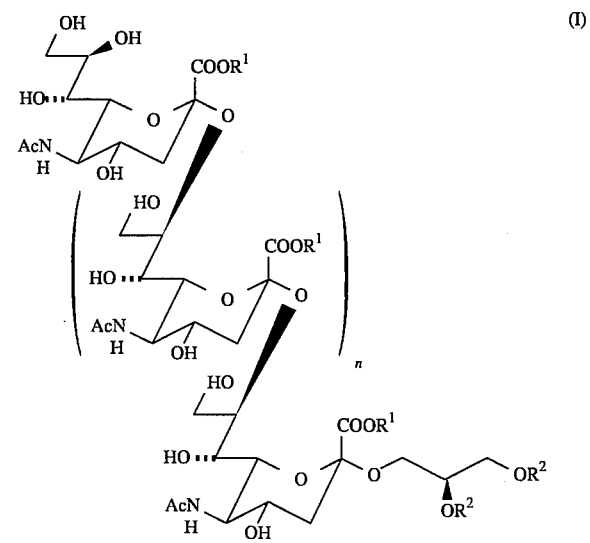

wherein each $R^1$ independently represents a group selected from the group consisting of a hydrogen atom and alkali metal atoms, each $R^2$ independently represents an alkyl group having 14 to 18 carbon atoms, Ac represents an acetyl group, and n represents an integer of from 0 to 20, and synthetic intermediates for their preparation useful as an immuno-stimulating agent, an antitumor agent, and a diagnostic and therapeutic agent for cancers.

4 Claims, No Drawings

OLIGOSIALYL-1,2-DIALKYL-SN-GLYCEROLS AND SYNTHETIC INTERMEDIATES FOR THEIR PREPARATION

TECHNICAL FIELD

The present invention relates to oligosialyl-1,2-dialkyl-sn-glycerols and synthetic intermediates for their preparation. More specifically, it relates to α2 →8 oligosialyl-1,2-dialkyl-sn-glycerols and synthetic intermediates for their preparation, and processes for preparing said compounds.

BACKGROUND ART

Various sugar chain structures containing a sialic acid have been found in gangliosides and glycoproteins. For example, some sialic acid-containing polysaccharides have been found in capsular components of certain pathogenic bacteria. The capsular polysaccharide isolated from Neisseria meningitidis Serotype C is composed of a single polymer consisting of N-acetylneuraminic acids connected with α2 → 9 bond. $^{13}$C NMR spectroscopic study has revealed that the polymer (at 8- or 9-position) has partially O-acetylated structures (A. K. Bhattachariee, H. J. Jennings, C. P. Kenny, A. Martin, I.C.P. Smith, J. Biol. Chem., 250, 1926–1932, 1975). In addition, it has been reported that the capsular polysaccharide isolated from Escherichia coli Bos 12 is also a hetero-polymer having both α2 →9 and α2 → 8 bonding structures and that the capsular polysaccharide isolated from Escherichia coli K1 is a homo-polymer having α2 →8 bonding structures (W. Egan, T. Y. Lui, D. Dorow, J. S. Cohem, J. D. Robine, E. C. Gotschlich, J. B. Robins, Biochemistry, 16, 3687–3692, 1977). Some of polysaccharides produced by bacteria have recently been found to have pharmacological activities such as immuno-stimulating activity and antitumor activity (E. C. Gotschlich, B. A. Franser, O. N. Shimura, J. B. Robbins, T. Y. Lui, J.Biol, Chem., 256, 8915–8921, 1981). They are substances of interest from their pharmacological activities.

However, any process for chemical preparation of oligosialic acids as well as aforementioned sialic acid-containing polysaccharides has not been reported to date.

Accordingly, an object of the present invention is to provide oligosialyl-1,2-dialkyl-sn-glycerols which are derivatives of oligosialic acids and synthetic intermediates for their preparation. In addition, the present invention provides a process for preparing said oligosialyl-1,2-dialkyl-sn-glycerols.

DISCLOSURE OF THE INVENTION

The inventors of the present invention succeeded in preparing oligosialyl-1,2-dialkyl-sn-glycerols by using an oligosialic acid as a starting material which was stereoselectively prepared by the condensation between a sugar-donative sialic acid introduced by a facilitative group at the 3-position and a suitably protected sugar-accepting sialic acid. The present invention was achieved on the basis of these findings. The present invention thus relates to oligosialyl-1,2-dialkyl-sn-glycerols represented by formula (I);

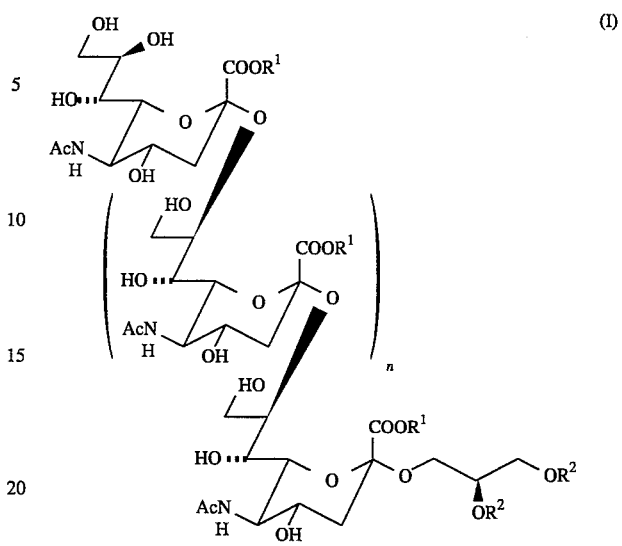

synthetic intermediates for preparing said oligosialyl-1,2-dialkyl-sn-glycerol represented by formulas (II) and (III):

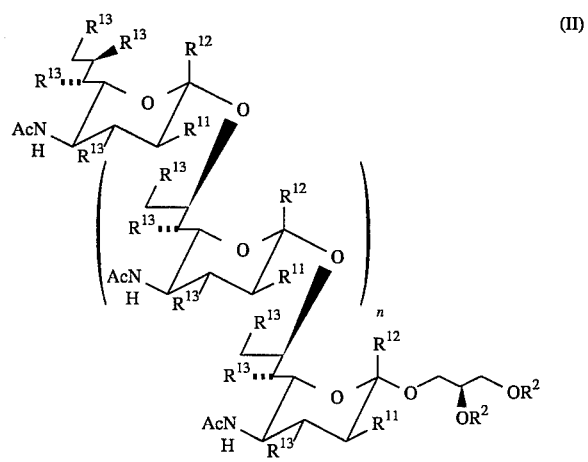

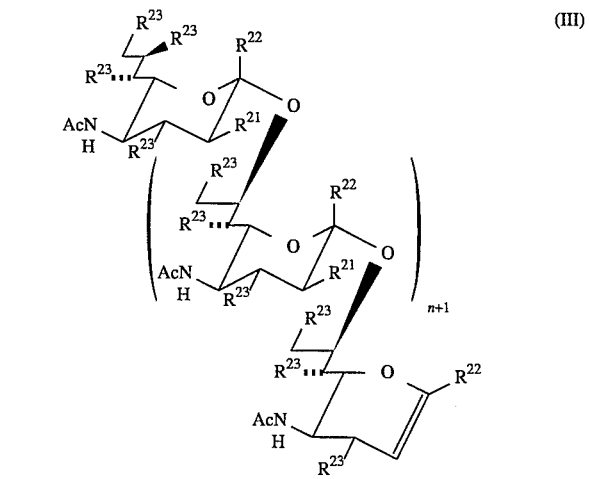

and a process for preparing said oligosialyl-1,2-dialkyl-sn-glycerol represented by formula (I) comprising the step of condensing a compound represented by formula (IV):

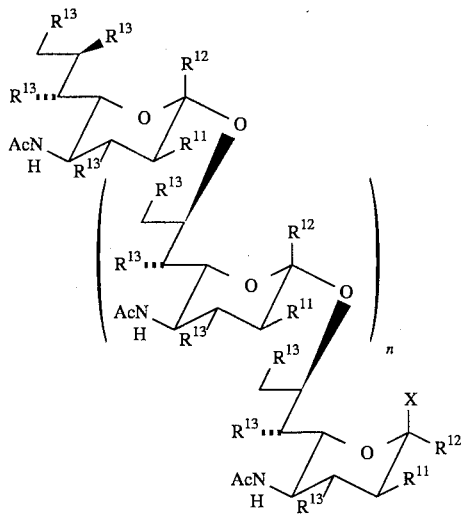

with a 1,2-dialkyl-sn-glycerol represented by formula (V):

to produce a synthetic intermediate represented by formula (II) for preparing said oligosialyl-1,2-dialkyl-sn-glycerol.

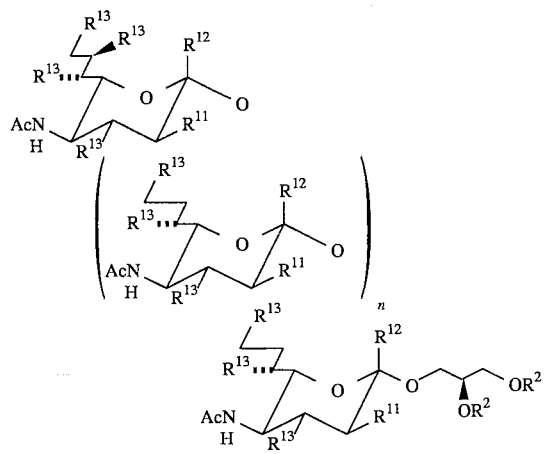

BEST MODE FOR CARRYING OUT THE INVENTION

In formula (I), each $R^1$ independently represents a radical selected from the group consisting of a hydrogen atom and alkali metal atoms. Among them, a hydrogen atom and a sodium atom are preferred. In formulas (I), (II), and (V), each $R^2$ independently represents an alkyl group having 14 to 18 carbon atoms. Among them, an alkyl group having 14 carbon atoms is prefered. Each $R^{11}$ in formulas (II) and (IV) and each $R^{2\,1}$ in formula (III) independently represents a substituent selected from the group consisting of thiophenyl group and selenylphenyl group. Among them, thiophenyl group is preferred. Each $^{1\,2}$ in formulas (II) and (IV) and each $R^{2\,2}$ in formula (III) independently represents a carboxyl group which may optionally be protected. More specifically, examples of protective groups include methyl group, benzyl group, and allyl group. However, they are not limited to these groups and may be selected from those apparent to one of ordinary skill in the art. Among these groups, methyl group is preferred. Each $R^{1\,3}$ in formulas (II) and (IV) and each $R^{2\,3}$ in formula (III) independently represents a hydroxyl group which may optionally be protected. More specifically, examples of protective groups include benzyloxy group, acetyloxy group, and triphenylmethyloxy group. However, they are not limited to these groups and may be selected from those apparent to one of ordinary skill in the art. Among these groups, benzyloxy group is preferred. X in formula (IV) represents a halogen atom which may be a fluorine atom, a chlorine atom, a bromine atom, or an iodine atom. Among them, a chlorine atom is preferred. In formulas (I) to (IV), n represents an integer of from 0 to 20. Among them, 0 and 1 are preferred.

For the condensation of the compound represented by formula (IV) with the dialkyl glycerol represented by formula (V), $Hg(CN)_2$—$HgBr_2$. AgOTf, $Cp_2HfCl_2$—AgOTf, $Cp_2ZrCl_2$—AgOTf or the like may be selected as a condensing agent. Among them, $Hg(CN)_2$—$HgBr_2$ is preferred. The aforementioned condensation reaction may be carried out for 4 to 18 hours at from −20° C. to room temperature under 760 mmHg (an ordinary pressure) in a solvent such as, for example, carbon tetrachloride, dichloromethane, 1,2-dichloroethane, or acetonitrile. According to a preferred embodiment in which $Hg(CN)_2$—$HgBr_2$ is used as the condensing agent, the above-described condensation reaction may be carried out for 4 to 18 hours at from −20° C. to room temperature under 760 mmHg in carbon tetrachloride as a solvent.

An example of the process for preparing the synthetic intermediates and the oligosialyl-1,2-dialkyl-sn-glycerols of the present invention will be explained in schemes set out below. However, the scope of the present invention is not limited to the following reaction schemes. In the schemes, Bn represents a benzyl group, Me represents a methyl group, Ac represents an acetyl group, and Ph represents a phenyl group.

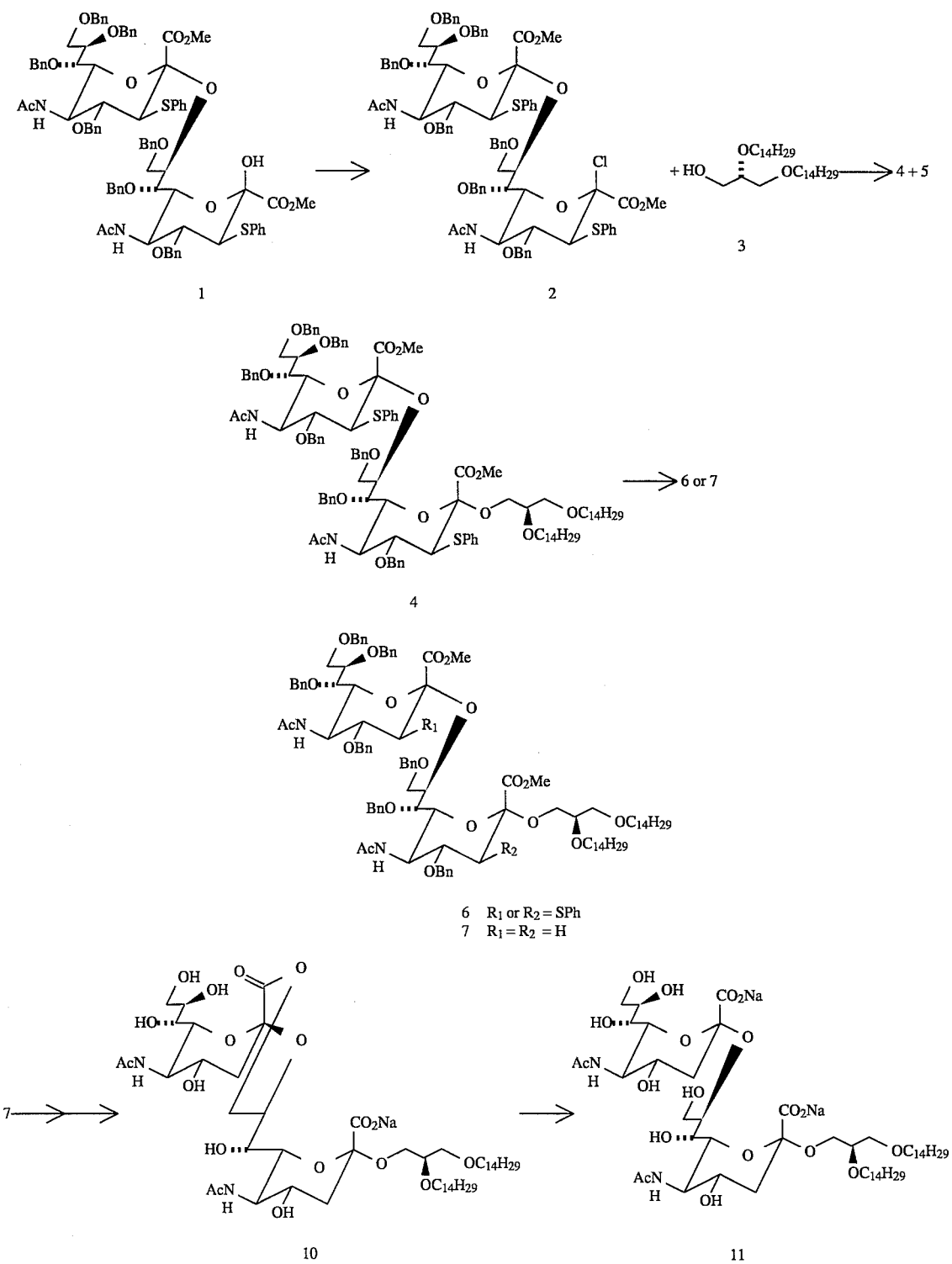

-continued
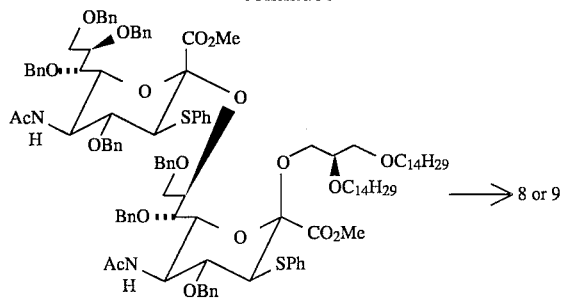
5
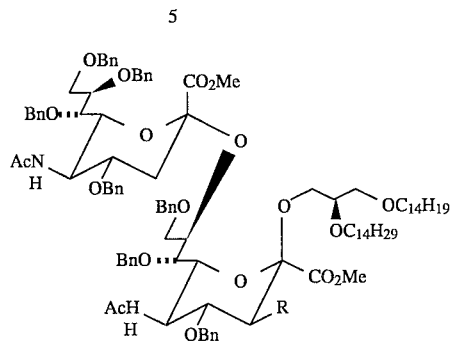
8  R = SPh
9  R = H
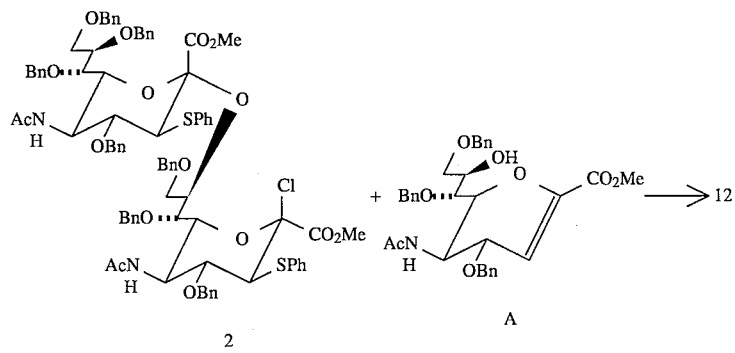
2                                         A
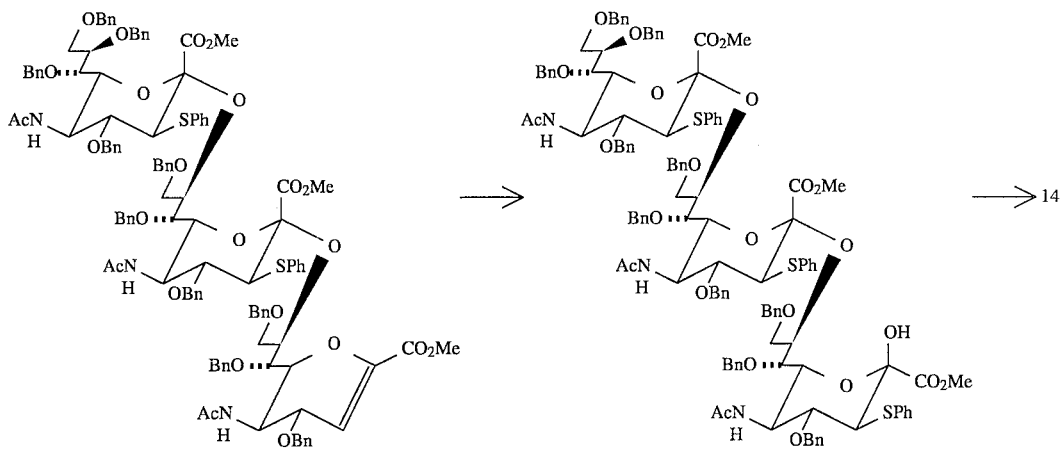
12                                        13

-continued
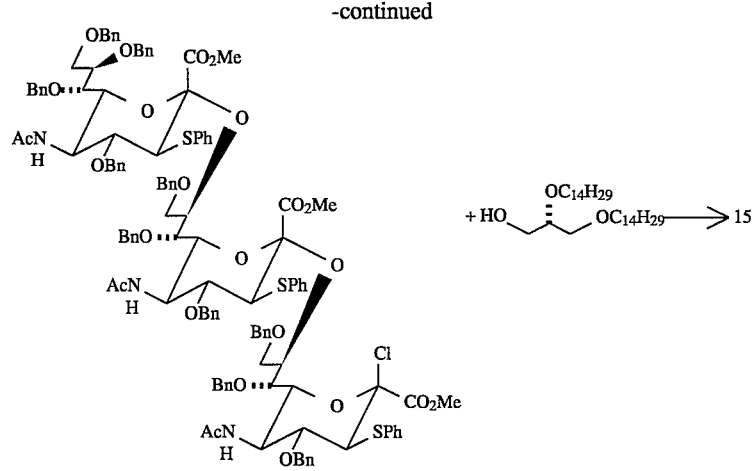
14
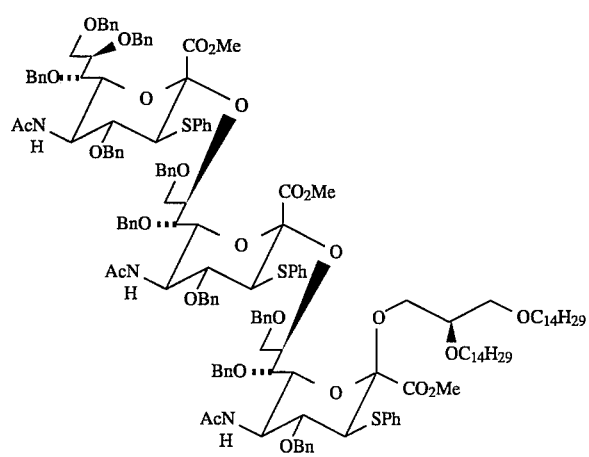
15
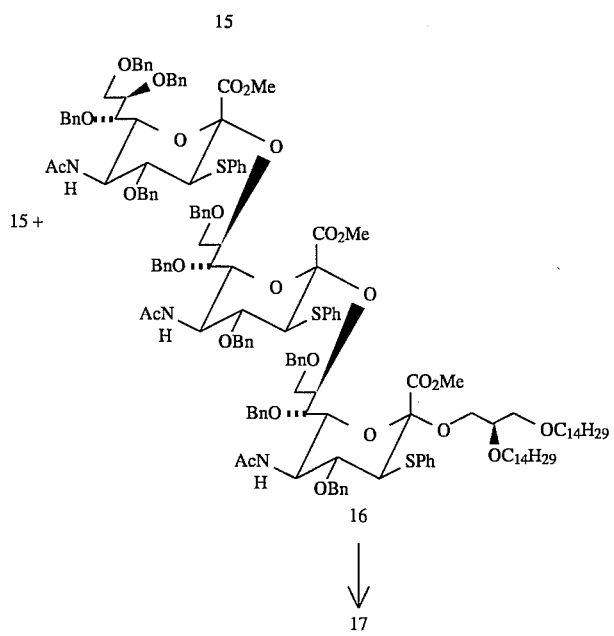

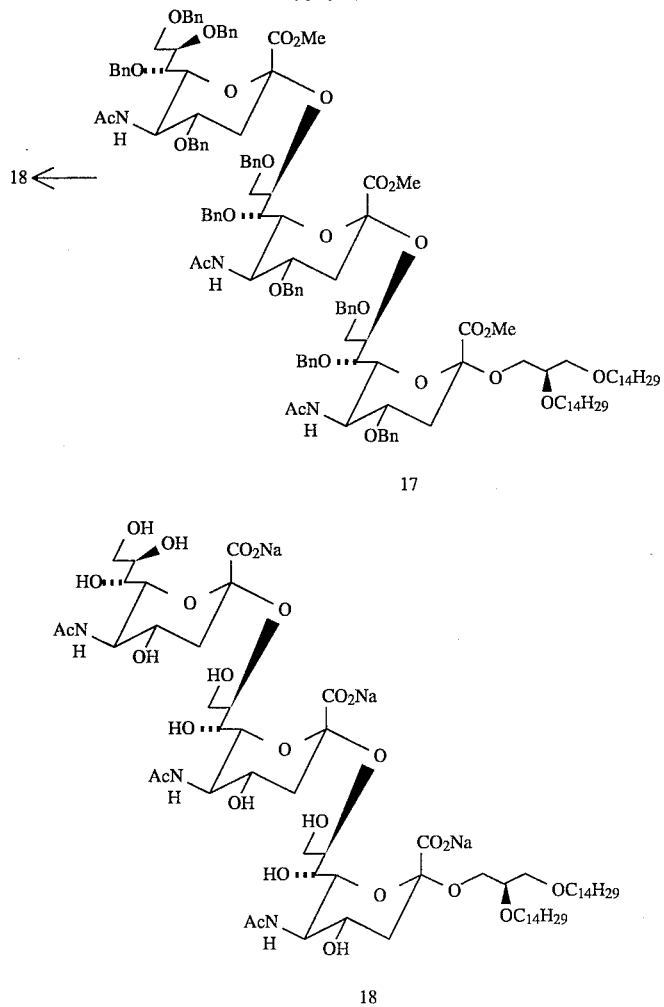

In the above-described schemes, reagents and reaction conditions preferably used are explained below, wherein A represents a catalyst, B represents a solvent, C represents a period of time, D represents a temperature, HMPT represents hexameth ylphosphoroustriamide, DMF represents dimethylformamide, AIBN represents azobisisobutyronitrile, THF represents tetrahydrofuran, NBS represents N-bromosuccinimide, and LDA represents lithium diisopropyl amine.

1. 1→2
 (1)
  A: CCl$_4$, HMPT
  B: THF
  C: 3.5 hours
  D: −10° C.
 (2)
  A: SOCl$_2$, +DMF
  B: CH$_2$Cl$_2$, Cl(CH$_2$)$_2$Cl, CH$_3$CN
  C: 30 minutes to overnight
  D: −20° C. to 40° C.
2. 2+3→4, 5
 (1)
  A: HgBr$_2$+Hg(CN)$_2$
  B: CCl$_4$
  C: 17 hours
  D: −10° C. to room temperature
 (2)
  A: AgOTf, Ag$_2$CO$_3$, AgCl$_4$
  B: CH$_2$Cl$_2$, Cl(CH$_2$)$_2$Cl, CH$_3$CN, CHCl$_3$, toluene, benzene
  C: 2 hours to overnight
  D: −40° C. to 60° C.
3. 4→6, 7 and 5→8, 9
 (1)
  A: AIBN, Ph$_3$SnH
  B: toluene
  C: 2 hours
  D: 80° C.
 (2)
  A: AIBN, n-Bu$_3$SnH, Raney-Ni
  B: benzene
  C: 1 hour to overnight
  D: 80° C. to 120° C.
4. 7→10
 (1)
  A: 10% Pd—C
  B: H$_2$O—CH$_3$OH C: overnight
D: room temperature
(2)
A: 5% Pd—C, Pd(OH)$_2$, Pd-black
B: CH$_3$OH, CH$_3$OH—AcOH, C$_2$H$_5$OH, C$_2$H$_5$OH—CH$_3$COOC$_2$H$_5$
C: 2 hours to overnight
D: room temperature to 60° C.
(3)
A: 0.025 N·NaOH
B: THF-CH$_3$OH
C: 2 hours
D: room temperature
(4)
A: no particular catalyst
B: CH$_3$OH
C: 2 hours to overnight
D: room temperature to 60° C.
5. 10→11
(1)
A: 0.2 N NaOH
B: THF - CH$_3$OH
C: 3 hours
D: room temperature
(2)
A: 0.2 to 1 N NaOH
B: CH$_3$OH
C: 2 hours to overnight
D: room temperature to 60° C.
6. 2+A →12
(1)
A: HgBr$_2$+Hg(CN)$_2$
B: CCl$_4$
C: 4 days
D: −10° C. to room temperature
(2)
A: AgoTf, Ag$_2$CO$_3$, AgClO$_4$, CH$_2$Cl$_2$, Cl(CH$_2$)$_2$Cl, CH$_3$CN, CHCl$_3$
B: toluene, benzene
C: 6 hours to 4 days
D: −40° C. to 60° C.
7. 12→13
(1)
A: NBS
B: CH$_3$CN—H$_2$O
C: 2.5 hours
D: room temperature
(2)
A: no particular catalyst
B: no particular solvent
C: 0.5 hour to overnight
D: room temperature to 70° C.
(3)
A: t-BuOK
B: t-BuOH-THF
C: 2 hours
D: −10° C.
(4)
A: NaH, LDA B: t-BuOH-DMF
C: 0.5 hour to overnight
D: −40° C. to room temperature
8. 13→14
(1)
A: CCl$_4$, HMPT
B: THF
C: 22 hours
D: −10° C. to room temperature
(2)
A: SOCl$_2$+DMF
B: CH$_2$Cl$_2$, Cl(CH$_2$)$_2$Cl, CH$_3$CN
C: 3 hours to overnight
D: −20° C. to 40° C.
9. 14+3→15+16
(1)
A: HgBr$_2$+Hg(CN)$_2$
B: CCl$_4$
C: 22 hours
D: −10° C. to room temperature
(2)
A: AgOTf, Ag$_2$CO$_3$, AgClO$_4$
B: CH$_2$Cl$_2$, Cl(CH$_2$)$_2$Cl, CH$_3$CN, CHCl$_3$, toluene, benzene
C: 30 minutes to overnight
D: −40° C. to 60° C.
10. 16→17
(1)
A: AIBN, Ph$_3$SnH
B: benzene
C: 1 hour
D: 80° C.
(2)
A: AIBN, n-BuSnH, Raney Ni
B: toluene
C: 1 hour to overnight
D: 80° C. to 120° C.
11. 17→18
(1)
A: 10% Pd-C
B: CH$_3$OH
C: overnight
D: room temperature
(2)
A: 5% Pd—C, Pd(OH)$_2$, Pd-black
B: H$_2$O—CH$_3$OH, H$_2$O—C$_2$H$_5$OH, C$_2$H$_5$OH
C: 2 hours to overnight
D: room temperature to 60° C.
(3)
A: 0.2 N NaOH
B: THF-CH$_3$OH
C: overnight
D: room temperature
(4)
A: 0.2N to 1N NaOH
B: CH$_3$OH
C: 2 hours to overnight
D: room temperature to 60° C.

A preferred embodiment of the present invention will be explained by way of examples set out below. However, the scope of the present invention is not limited to these examples (numbers of the compounds in the examples correspond to the numbers of the compounds in the schemes set out above).

In the examples, compounds 1 and 2 are described by Ito et al. ( Y. Ito, M. Numata, M. Sugimoto, and T. Ogawa, J. Am. Chem. Soc., 1989, 111, pp. 8508–8510); compound 3 is described by Baer et al. (E. Baer and N. Z. Stanacev, J. Biol. Chem., 240, 1965, pp. 44–48), by Kates (M. Kates, T. H. Chem, and N. Z. Stamacev, Biochemistry, 2, 1963, pp. 394–397), and by Ogawa et al. (T. Ogawa and K. Beqqu, Agric. Biol. Chem., 46, 1982, pp. 255–262); and compound A is described by Ito et al. (Y. Ito, M. Numata, M. Sugimoto, and T. Ogawa, J. Am. Chem. Soc., 1989, 111, pp. 8508–8510). In these experiments, the aforementioned compounds were prepared according to processes described in the above-described documents.

EXAMPLE 1: 1→2

A mixture of compound 1 (222 gm, 0.15 mmol), carbon tetrachloride (200 μl, 2.08 mmol), hexamethylphosphoroustriamide (250 μl, 1.38 mmol) and dry tetrahydrofuran (3 ml) was stirred for 3.5 hours under ice-cooling. After extraction with ethyl acetate, the extract was washed with diluted hydrochloric acid and then with saturated aqueous sodium chloride solution. After the organic layer was dried over magnesium sulfate, the solvent was removed by distillation, and then the residue was purified by flash column chromatography (toluene/acetone=4:1) to give compound 2 (213 mg, 95%).
Compound 2
Rf=0.46 (toluene/acetone=9:2)
$[\alpha]_D$+13.3° (24° C., c=1.5, chloroform)

|      |       | C (%) | H (%) | N (%) |
|------|-------|-------|-------|-------|
| Anal.| Calcd.| 68.60 | 6.13  | 1.97  |
|      | Found | 68.33 | 6.00  | 1.87  |

NMR (δ) 7.53–7.04 (m, 45H, aromatic protons) 4.919 (d, J=11.0 Hz, NHAc ) 4.915 (d, J=11.2 Hz, NHAc ) 3.599, 3.496 (2s, 6H, 2×CO$_2$ C H$_3$) 1.659, 1.255 (2s, 6H, 2×NH-COC H$_3$)

EXAMPLE 2: 2+3→4+5

A mixture of compound 3 (470 mg, 0.97 mmol), Hg(CN)$_2$ (156 mg, 0.62 mmol), HgBr$_2$ (84 mg, 0.23 mmol), activated molecular sieves 4A (1 g), and dry carbon tetrachloride (5 ml) was stirred under ice-cooling under nitrogen atmosphere, and then a solution of compound 2 (290 mg, 0.194 mmol) in 10 ml of carbon tetrachloride was added. The mixture was slowly warmed up to room temperature and then stirred for 17 hours. The reaction mixture was filtered using Celite, and the filtrate was washed successively with 10% potassium iodide solution, saturated aqueous sodium bicarbonate solution, and saturated aqueous sodium chloride solution. The organic layer was dried over magnesium sulfate, and then the solvent was removed by distillation. The residue was purified by gel filtration using SX-3 to give a mixture of compounds 4 and 5 (285 mg). The resulting mixture was purified by column chromatography (toluene/acetone=9: 1) to give compound 4 (204 mg, 54%) and compound 5 (31 mg, 8%).
Compound 4
Rf=0.32 (toluene/acetone=6:1)
$[\alpha]_D$ +22.3° (23° C., c=2.2, CHCl$_3$)
Anal. C$_{116}$H$_{152}$N$_2$O$_{19}$S$_2$

|        | C (%) | H (%) | N (%) |
|--------|-------|-------|-------|
| Calcd. | 71.72 | 7.89  | 1.44  |
| Found  | 71.52 | 7.84  | 1.39  |

NMR (δ) 7.53–7.06 (m, 45H, aromatic protons) 3.753, 3.617 (2s, 6H, 2×CO$_2$ C H$_3$) 1.644, 1.511 (2s, 6H, 2×NH COCH$_3$) 1.253 (br-s, 48H, CH$_2$) 0.878 (t, 6H, J=6.7 Hz, CH$_3$)
Compound 5
Rf=0.50 (toluene/acetone=6:1)
$[\alpha]_D$+16.1° (23° C., c=0.8, CHCl$_3$)
NMR (δ) 7.58–6.92 (m, 45H, aromatic protons) 4.959 (d, 1H, J=11.6 Hz, NHAc ) 4.824 (d, 1H, J=11.0 Hz, NHAc ) 3.455, 3.451 (2s, 6H, 2×CO$_2$CH$_3$) 1.25 (br-s, 48H, CH$_2$) 0.878 (t, 6H, J=6.7 Hz, CH$_3$)

EXAMPLE 3: 4→6 or 7

A mixture of compound 4 (115 mg, 59 μmol), AIBN (6 mg, 37 μ mol), 1 N triphenyltinhydride in toluene (1 ml), and dry toluene (4 ml) was refluxed for 2 hours. The solvent was removed and the residue was purified by using SX-4 (toluene). The reaction procedure and post-reaction treatment were repeated additional three times, and the product was finally purified using preparative TLC (toluene/acetone=5:1) to give compound 6 (8.5 mg, 8%) and compound 7 ( 48 mg, 47% ).
Compound 7
Rf=0.30 (toluene/acetone=5:1)
$[\alpha]_D$+2.0° (23° C., c=1.1, CHCl$_3$)
Anal. C$_{104}$H$_{144}$N$_2$O$_{19}$

|        | C (%) | H (%) | N (%) |
|--------|-------|-------|-------|
| Calcd. | 72.36 | 8.41  | 1.62  |
| Found  | 72.15 | 8.32  | 1.63  |

NMR (δ, 55° C., CDCl$_3$) 7.52–7.12 (m, 35H, aromatic protons) 5.002 (d, 1H, J=9.8 Hz, NHAc ) 4.935 (d, 1H, J=10.7 Hz, NHAc ) 3.720, 3.547 (2s, 6H, 2×C O$_2$ C H$_3$) 2.768 (dd, 1H, H-3b, eq) 2.641 (dd, 1H, J=4.6, 12.8 Hz, H-3a, eq) 1.956 (t, 1H, J=12.8 Hz, H-3a, ax) 1.802, 1.590 (2s, 6H, 2×NHCOC H$_3$) 1.25 (br-s, 48H, CH$_2$) 0.878 (t, 6H, J=6.7 Hz, CH$_3$)

EXAMPLE 4: 5→8 or 9

A mixture of compound 5 (30 mg, 15 μmol), AIBN (1.5 mg, 10 μ mol), 0.94 N triphenyltinhydride in benzene (200 μl ), and dry benzene (500 μl ) was refluxed for 1.5 hours. The solvent was removed by distillation and the residue was purified using SX-4 (toluene.). This reaction procedure and post-reaction treatment were repeated additional 5 times, and the product was finally purified by column chromatography (hexane/ethyl acetate=3:1) to give compound 8 (3 mg, 11%) and compound 9 (3 mg, 11%).
Compound 8
Rf=0.42 (toluene/acetone =5:1)
NMR (δ) 7.50–7.05 (m, 4 OH, aromatic protons) 5.492 (d, 1H, J=7.9 Hz, NHCOC H$_3$) 5.425 (d, 1H, J=7.9 Hz, NHCOC H$_3$) 3.497, 3.493 (2s, 6H, 2×C O$_2$ C H$_3$) 2.704 (dd, 1H, J=4.2, 12.5 Hz, H-3b eq) 1.23 (br-s, 48H, CH$_2$) 0.876 (t, 6H, J=7.0 Hz, CH$_3$)

Compound 9

Rf=0.38 (toluene/acetone =5:1)

NMR (δ) 7.50–7.10 (m, 35H, aromatic protons) 5.458 (d, 1H, J=7.6 Hz, NHCOC H$_3$) 5.416 (d, 1H, J=8.6 Hz, NHCOC H$_3$) 3.698, 3.536 (2s, 6H, 2×C O$_2$ C H$_3$) 2.742 (dd, 1H, J=3.3, 11.9 Hz, H-3b eq) 1.23 (br-s, 48H, CH$_2$) 0.878 (t, 6H, J=7.0 Hz, CH$_3$)

Example 5: 7→10

A mixture of compound 7 (40 mg, 23 μmol), 10% Pd—C (40 mg), and 30% aqueous methanol (6 ml) was reduced overnight by catalytic hydrogenation. The reaction mixture was filtered using Celite and the filter cake was well washed with aqueous methanol. The filtrate was concentrated under reduced pressure and dried several times by azeotropic distillation using toluene. To the residue, 1 ml THF/CH$_3$OH solution (1:1) and 1 ml of 0.025N aqueous sodium hydroxide solution were added, and then the mixture was stirred for 2 hours at room temperature. The solvent was removed by distillation and the residue was purified by gel filtration (LH-20, CHCl$_3$/CH$_3$OH/H$_2$O=60:30:5) to give 7 mg of compound 10 (27%).

Compound 10

Rf=0.26 (CHCl$_3$/CH$_3$OH/H$_2$O=12:6:1)

NMR (δ, CD$_3$OD) 2.863 (dd, 1H, J=4.1, 12.8 Hz, H-3b eq) 2.661 (ddd, 1H, J=1.5, 4.4, 12.9 Hz, H-3a eq) 2.045, 2.019 (2s, 6H, 2×NHCOC H$_3$) 1.287 (br-s, 48H, CH$_2$) 0.896 (t, 6H, J=7.0 Hz, CH$_3$)

Compound 6: 10→11

A mixture of compound 10 (4 mg, 3.7 μmol), 2 ml of THF/CH$_3$OH (1:1), and 0.2 ml of 0.2N aqueous sodium hydroxide solution was stirred for 3 hours at room temperature. The solvent was removed by distillation and the residue was purified by gel filtration (LH-20, CHCl$_3$/CH$_3$OH/H$_2$O= 60:30:5) to give 4 mg of compound 11 (96.4%).

Compound 11

Rf=0.20 (CHCl$_3$/CH$_3$OH/H$_2$O=12:6:1)

NMR (δ, CD$_3$OD) 2.045, 2.012 (2s, 6H, 2×NHCOC H$_3$) 0.895 (t, 6H, J=6.7 Hz, CH$_3$)

EXAMPLE 7: 2+11→12

A mixture of compound A (147 mg, 26 μmol), Hg(CN)$_2$ (96 mg, 38 μmol), HgBr$_2$ (46 mg, 13 μmol), activated molecular sieves 4A (1 g), and dry carbon tetrachloride (3 ml) was stirred under ice-cooling under nitrogen atmosphere, and then 2 ml solution of compound 2 (190 mg, 13 μmol) in carbon tetrachloride was added. The mixture was gradually warmed up to room temperature and then stirring was continued for 4 days. The reaction mixture was filtered using Celite, and the filtrate was washed succesively with 10% potassium iodide solution, saturated aqueous sodium bicarbonate, and saturated aqueous sodium chloride solution. The organic layer was dried over magnesium sulfate, and then the solvent was removed by distillation. The residue was purified by gel filtration using SX-3 (toluene) to give compound 12 (91 mg, 41%). Compound 11 was recovered (109 mg, 74%).

Compound 12

Rf=0.37 (toluene/acetone=4:1)

[α]$_D$+7.8° (24° C., c=0.85, CHCl$_3$)

Anal. C$_{118}$H$_{125}$N$_3$O$_{24}$S$_2$·H$_2$O

|  | C (%) | H (%) | N (%) |
| --- | --- | --- | --- |
| Calcd. | 69.09 | 6.24 | 2.08 |
| Found | 68.76 | 6.11 | 1.98 |

NMR (δ) 7.60–6.95 (m, 60H, aromatic protons) 5.865 (br-s, 1H, H-3a) 5.40–5.15 (br, 1H, NHAc ) 4.897 (d, 1H, J=12.2 Hz, NHAc ) 4.755 (d, 1H, J=11.0 Hz, NHAc ) . 3.759, 3.609, 3.772 (3s, 9H, 3×CO$_2$ C H$_3$) 1.683, 1.610, 1.589 (3s, 9H, 3×NHCOC H$_3$)

EXAMPLE 8: 12→13

A mixture of compound 12 (91 mg, 45 μmol), NBS (11 mg, 61 μ mol), acetonitrile (2 ml), and 0.3 ml of water was stirred for 2.5 hours at room temperature. After the solvent was removed by distillation, azeotropic distillation was carried out several times using toluene. The residue was purified by silica gel chromatography (hexane/acetone=4:3) to give the bromohydrine compound. Thiophenol (10 μl, 9 μmol) was dissolved in t-butanol/THF (1:1, 1 ml), and a solution of potassium t-butoxide in t-butanol (1M, 14 μl) was added with stirring under ice-cooling. After 10 minutes, a solution of the above-obtained bromohydrine in THF (3 ml) was added and stirring was continued for additional 2 hours. The reaction mixture was diluted with ether, and washed with 0.2N aqueous NaOH solution and then with saturated aqueous sodium chloride solution. The organic layer was dried over magnesium sulfate, and the solvent was removed by distillation. Toluene (2 ml) was added to the residue and 1,8-diazabicyclo[5.4.0]-7-undecene (1 μl, 6.7 μmol) was added with stirring under ice-cooling, and then stirring was continued for additional 1 hour. The reaction mixture was diluted with ethyl acetate, and then washed successively with 0.1N aqueous HCl solution, saturated aqueous sodium bicarbonate solution, and saturated aqueous sodium chloride solution. The organic layer was dried over magnesium sulfate, and the solvent was removed by distillation. The residue was purified by silica gel column chromatography (toluene/acetone=8:1) to give compound 13 (77 mg, 80%).

Compound 13

Rf=0.41 (toluene/acetone=4:1)

[α]$_D$+21.6° (22° C., c=1.0, CHCl$_3$)

Anal. C$_{124}$H$_{131}$N$_3$O$_{25}$S$_3$·4H$_2$O

|  | C (%) | H (%) | N (%) |
| --- | --- | --- | --- |
| Calcd. | 66.74 | 6.28 | 1.88 |
| Found | 66.69 | 5.93 | 1.92 |

NMR (δ) 7.55–6.95 (m, 65H, aromatic protons) 3.775, 3.629, 3.602 (3s, 9H, 3×C O$_2$ C H$_3$) 1.637, 1.616, 1.508 (3s, 9H, 3×NHCOC H$_3$)

EXAMPLE 9: 13→14

A mixture of compound 13 (81 mg, 38 μmol), carbon tetrachloride (150 μl, 1.56 mmol), and hexamethylphosphoroustriamide (70 μl, 385 μmol), and dry THF (5 ml) was stirred for 22 hours at from ice-cooling temperature to room temperature. The mixture was diluted with ethyl acetate, and then washed successively with diluted hydrochloric acid and with saturated aqueous sodium chloride solution. The organic layer was dried over magnesium sulfate and the solvent was removed by distillation. The residue was purified by flash column chromatography (toluene/acetone =4:1) to give compound 14 (81 mg, 99%).

Compound 14

Rf=0.41 (toluene/acetone=5:1)

$[\alpha]_D$+ 10.9° (23° C., c=1.0, $CHCl_3$)

Anal. $C_{124}H_{130}N_3O_{24}S_3Cl$

|        | C (%)  | H (%) | N (%) |
|--------|--------|-------|-------|
| Calcd. | 68.38  | 6.02  | 1.93  |
| Found  | 67.78  | 6.27  | 1.80  |

NMR (δ) 7.55–6.95 (m, 65H, aromatic protons) 4.902 (d, 1H, J=11.3 Hz, NHAc ) 4.858 (d, 1H, J=11.0 Hz, NHAc ) 4.794 (d, 1H, J=11.3 Hz, NHAc ) 3.767, 3.601, 3.433 (3s, 9H, 3×C $O_2$ C $H_3$)

EXAMPLE 10: 14+3→15+16

A mixture of compound 3 (44 mg, 90 μmol), $Hg(CN)_2$ (15 mg, 60 μ mol), $HgBr_2$ (8 mg, 22 μmol), activated molecular sieves 4A (200 mg), and dry carbon tetrachloride (1 ml) was stirred under ice-cooling under nitrogen atmosphere, and 2 ml solution of compound 14 (40 mg, 18 μmol) in carbon tetrachloride was added. The mixture was slowly warmed up to room temperature. After stirring was continued for 22 hours, the reaction mixture was filtered using Celite and the filtrate was washed successively with 10% potassium iodide solution, saturated aqueous sodium bicarbonate solution, and saturated aqueous sodium chloride solution. The organic layer was dried over magnesium sulfate and the solvent was removed by distillation. The residue was purified by gel filtration using SX-3 to give 37 mg of a mixture of compounds 15 and 16. The mixture was purified by silica gel column chromatography (toluene/acetone=4:1) to give a mixture of compounds 15 and 16 (19 mg) and purified compound 16 (14 mg, 29%). The mixture of compounds 15 and 16 (19 mg) was purified by preparative TLC (toluene/acetone=5:1) to give compound 15 (1 mg, 2%) and compound 16 (12 mg, 25%).

Compound 15

Rf=0.44 (toluene/acetone=5:1)

Compound 16

Rf=0.48 (toluene/acetone=4:1)

$[\alpha]_D$+7.8° (22° C., c=1.3, $CHCl_3$)

NMR (δ) 7.55–6.90 (m, 65H, aromatic protons) 3.779, 3.679, 3.596 (3s, 9H, 3×$CO_2$ C $H_3$) 1.253 (br-s, 48H, $CH_2$) 0.878 (t, 6H, $CH_3$)

EXAMPLE 11: 16→17

A mixture of compound 16 (10 mg, 3.8 μmol), 1N solution of triphenyltinhydride in benzene (200 μl), 25 μl of a solution of AIBN prepared beforehand (AIBN 20 mg/benzene 500 μl), and 300 μl of benzene was refluxed. To the reaction mixture, 25 μl of the above described AIBN solution in benzene was added (4 times) at every one hour under reflux, and finally 1N solution of triphenyltinhydride in benzene (200 μl) and AIBN solution in benzene (25 μl) were added and reflux was continued for additional one hour. Insoluble materials were removed by filtration and the filter cake was well washed with ethyl acetate. The solvent was removed by distillation and the residue was purified using SX-3 (toluene). The resulting crude compound 17 was purified by preparative TLC (ethyl acetate/n-hexane=1:1) to give compound 17 (6.2 mg, 71%).

Compound 17

Rf=0.33 (ethyl acetate/n-hexane=1:1) .

$[\alpha]_D$+0.89° (22° C., c=0.4, $CHCl_3$)

NMR (δ) 7.50–7.10 (m, 50H, aromatic protons) 3.845, 3.732, 3.555 (3s, 9H, 3×C $O_2$ C $H_3$) 2.712 (br-d, 2H, J=12.8 Hz, H-3b eq, H-3c eq) 2.602 (dd, 1H, J=4.6, 13.1 Hz, H-3a eq) 1.837, 1.763, 1.604 (3s, 9H, 3×NHCOC $H_3$) 1.25 (br-s, 48H, $CH_2$) 0.878 (t, 9H, J=6.7 Hz, $CH_3$)

EXAMPLE 12: 17→18

A mixture of compound 17 (5 mg, 2.2 μmol), 10% Pd-C (10 mg), and 5 ml of $CH_3OH$ was reduced overnight by catalytic hydrogenation at room temperature. The catalyst was removed and well washed with $CH_3OH$. The solvent was removed by distillation, and to the residue, 0.3 ml of a mixed solvent of THF/$CH_3OH$ (1:1) and 0.2N aqueous sodium hydroxide solution were added and then stirring was continued overnight at room temperature. The solvent was removed by distillation, and the residue was purifed using LH-20 ($CHCl_3$:$CH_3OH$: $H_2O$ =60:30:5) to give 2.4 mg of compound 18 (80%).

Compound 18

Rf=0.09 ($CHCl_3$/$CH_3OH$/$H_2O$ =12:6:1)

NMR ($CD_3OD$, δ) 2.033, 2.018 (2s, 9H, 3×NHCOC $H_3$) 0.896 (t, 6H, J=6.7 Hz, $CH_3$)

INDUSTRIAL APPLICABILITY

By using the synthetic intermediates for preparing oligosialyl-1,2-dialkyl-sn-glycerol of the present invention, sialic acid-containing polysaccharides can efficiently be prepared.

Oligosialyl-1,2-dialkyl-sn-glycerol of the present invention and sialic acid-containing polysaccharides prepared from the synthetic intermediates of the present invention for preparing oligosialyl-1,2-dialkyl-sn-glycerol are useful compounds which may be used as immuno-stimulating agents, antitumor agents, diagnostics and therapeutic agents for cancers.

What is claimed is:

1. An oligosialyl-1,2-dialkyl-sn-glycerol represented by the following formula (I):

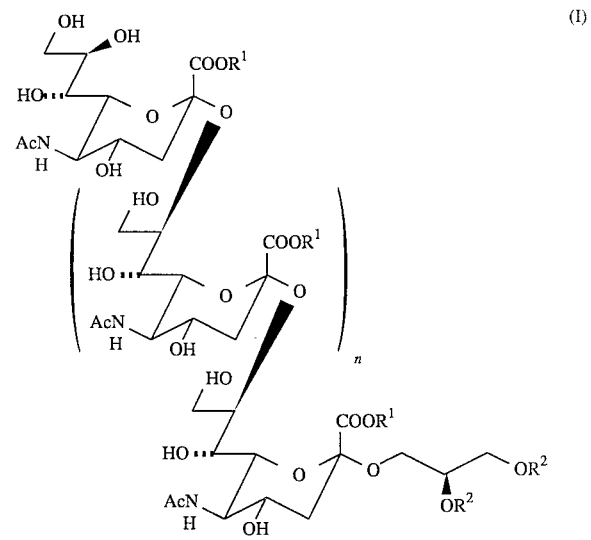

wherein each $R^1$ independently represents a group selected from the group consisting of a hydrogen atom and alkali metal atoms, each $R^2$ independently represents an alkyl group having 14 to 18 carbon atoms, Ac represents an acetyl group, and n represents an integer of from 0 to 20.

2. A synthetic intermediate represented by the following formula (II) for preparing an oligosialyl-1,2-dialkyl-sn-glycerol:

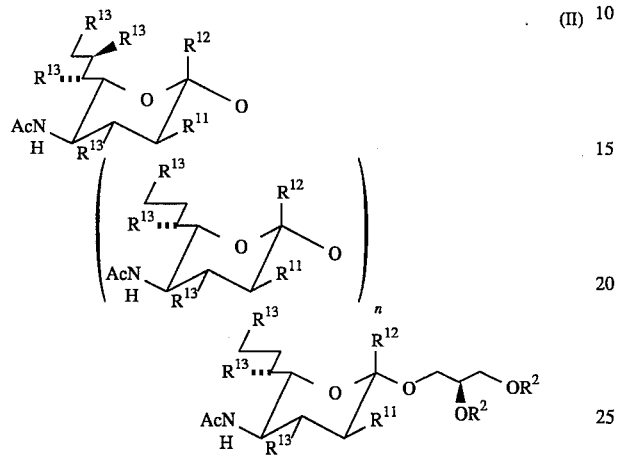
(II)

wherein each $R^{11}$ independently represents a group selected from the group consisting of thiophenyl group and selenylphenyl group, each $R^{12}$ independently represents a carboxyl group, each $R^{13}$ independently represents a hydroxyl group which may optionally be protected, each $R^2$ independently represents an alkyl group having 14 to 18 carbon atoms, Ac represents an acetyl group, and n represents an integer of from 0 to 20.

3. A synthetic intermediate represented by the following formula (III) for preparing an oligosialyl-1,2-dialkyl-sn-glycerol:

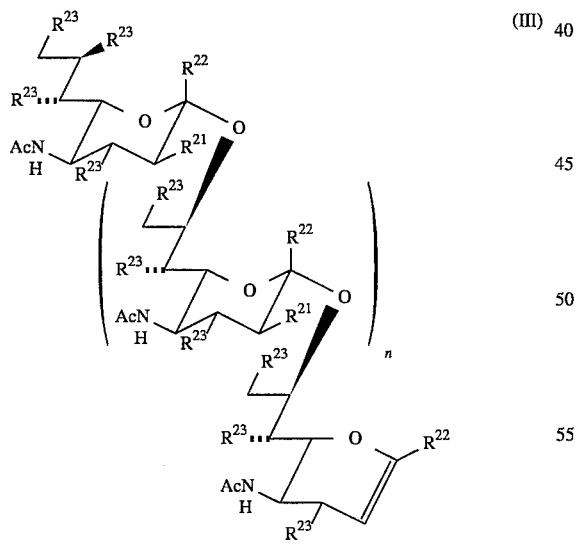
(III)

wherein each $R^{21}$ represents a group selected from the group consisting of thiophenyl group and selenylphenyl group, each $R^{22}$ independently represents a carboxyl group, each $R^{23}$ independently represents a hydroxyl group, Ac represents an acetyl group, and n represents an integer of from 0 to 20.

4. A process for preparing an oligosialyl-1,2-dialkyl-sn-glycerol according to claim 1 comprising the step of condensing a compound represented by the following formula (IV):

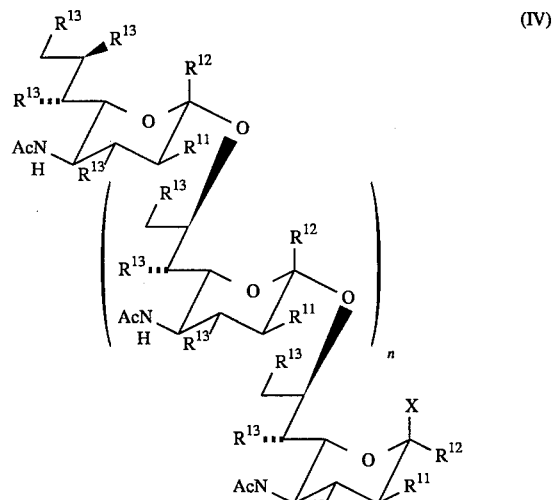
(IV)

wherein each $R^{11}$ independently represents a group selected from the group consisting of thiophenyl group and selenylphenyl group, each $R^{12}$ independently represents a carboxyl group, each $R^{13}$ independently represents a hydroxyl group, X represents a halogen atom, Ac represents an acetyl group, and n represents an integer of from 0 to 20, with a 1,2-dialkyl-sn-glycerol represented by the following formula (V):

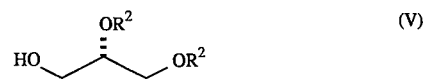
(V)

wherein each $R^2$ independently represents an alkyl group having 14 to carbon atoms to produce a synthetic intermediate for preparing an oligosialyl-1,2-dialkyl-sn-glycerol represented by the following formula (II):

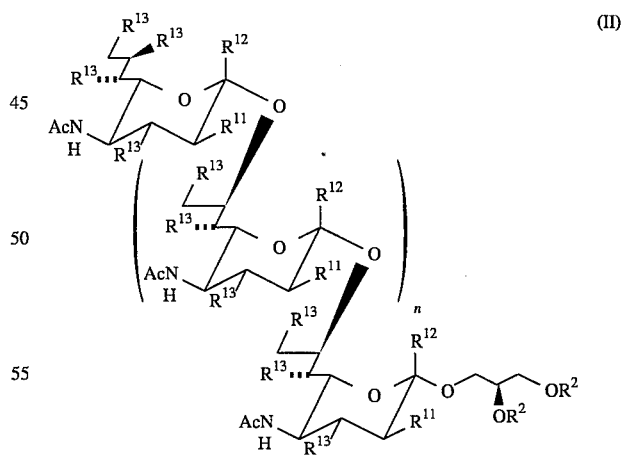
(II)

wherein each $R^{11}$ independently represents a group selected from the group consisting of thiophenyl group and selenylphenyl group, each $R^{12}$ independently represents a carboxyl group, each $R^{13}$ independently represents a hydroxyl group, each $R^2$ independently represents an alkyl group having 14 to 18 carbon atoms, Ac represents an acetyl group, and n represents an integer of from 0 to 20.

* * * * *

UNITED STATES PATENT AND TRADEMARK OFFICE
CERTIFICATE OF CORRECTION

PATENT NO. : 5,470,962
DATED : November 28, 1995
INVENTOR(S) : Tomoya OGAWA et al.

It is certified that error appears in the above-indentified patent and that said Letters Patent is hereby corrected as shown below:

On the title page, Item [86], the PCT number, should read:
--PCT/JP92/00249--

Signed and Sealed this

Twelfth Day of March, 1996

Attest:

BRUCE LEHMAN

*Attesting Officer*   *Commissioner of Patents and Trademarks*